(12) United States Patent
Elliott et al.

(10) Patent No.: US 8,129,186 B2
(45) Date of Patent: Mar. 6, 2012

(54) CHOROID PLEXUS PREPARATION AND USES THEREOF

(75) Inventors: Robert Bartlett Elliott, Auckland (NZ); Stephen John Martin Skinner, Auckland (NZ); Livia Del Carmen Escobar Orellana, Auckland (NZ); Christopher Thanos, Cumberland, RI (US)

(73) Assignee: Neurotrophincell Pty, Limited, Sydney (AU)

( * ) Notice: Subject to any disclaimer, the term of this patent is extended or adjusted under 35 U.S.C. 154(b) by 532 days.

(21) Appl. No.: 11/911,961

(22) PCT Filed: Apr. 18, 2006

(86) PCT No.: PCT/NZ2006/000075
§ 371 (c)(1),
(2), (4) Date: Apr. 28, 2008

(87) PCT Pub. No.: WO2006/112734
PCT Pub. Date: Oct. 26, 2006

(65) Prior Publication Data
US 2008/0286864 A1    Nov. 20, 2008

(30) Foreign Application Priority Data
Apr. 18, 2005  (NZ) ..................................... 536009

(51) Int. Cl.
*C12N 5/02* (2006.01)
(52) U.S. Cl. ......... 435/373; 435/384; 435/391; 435/368
(58) Field of Classification Search .................. None
See application file for complete search history.

(56) References Cited

U.S. PATENT DOCUMENTS

| | | | |
|---|---|---|---|
| 6,322,804 B1 | 11/2001 | Dionne et al. | |
| 6,372,494 B1 * | 4/2002 | Naughton et al. | 435/391 |
| 2004/0213768 A1 | 10/2004 | Elliott et al. | |
| 2005/0042746 A1 | 2/2005 | Garkavenko | |
| 2005/0265977 A1 | 12/2005 | Elliott et al. | |
| 2009/0075375 A1 | 3/2009 | Elliott et al. | |
| 2009/0162325 A1 | 6/2009 | Elliott et al. | |

FOREIGN PATENT DOCUMENTS

| | | |
|---|---|---|
| WO | 00/66188 | 11/2000 |
| WO | 0066188 | 11/2000 |
| WO | 0152871 A1 | 7/2001 |
| WO | 0232437 A1 | 4/2002 |
| WO | 2006132548 A1 | 12/2006 |

OTHER PUBLICATIONS

Aleshire SL et al. "Choroid plexus as a barrier to immunoglobulin delivery into cerebrospinal fluid". J Neurosurg. 63:593-7, 1985.
Borlongan, C.V., et. al. (Jul. 2004) "CNS Grafts of Rat Choroid Plexus Protect Against Cerebral Ischemia in Adult Rats." Neuroreport, 15(10):1543-7.
Fukuda A, Deshpande SB, Shimano Y, Nishino H "Astrocytes are more vulnerable than neurons to cellular Ca2+ overload induced by a mitochondrial toxin, 3-nitropropionic acid" Neuroscience 87:497-507, 1998.
Holm, N.R., et. al. (1994) "Gene Expression and Secretion of Insulin-Like Growth Factor-II and Insulin-Like Growth Factor Binding Protein-2 From Cultured Sheep Choroid Plexus Epithelial Cells." Molecular Brain Research 21:67-74.
Hosoya K, Hori S, Ohtsuki S, Terasaki T, 2004. A new in vitro model for blood-cerebrospinal fluid barrier transport studies: an immortalized choroid plexus epithelial cell line derived from the tsA58 SV40 large T-antigen gene transgenic rat. Adv Drug Deliv Rev. 56(12):1875-85.
Johanson CE et al "Choroid plexus recovery after transient forebrain ischemia: role of growth factors and other repair mechanisms". Cell Mol Neurobiol. 20: 197-216, 2000.
Watanabe, Y., et. al. (May 13, 2005) "Conditioned Medium of the Primary Culture of Rat Choroid Plexus Epithelial (Modified Ependymal) Cells Enhances Neurite Outgrowth and Survival of Hippocampal Neurons" Neuroscience Letters 379:158-63.
Zheng W, Zhao Q (2002) "Establishment and characterization of an immortalized Z310 choroidal epithelial cell line from murine choroid plexus." Brain Res. 958(2):371-80.
U.S. Appl. No. 11/916,963 for "Cell Implantations to Prevent and/or Treat Autoimmune Disease" filed Dec. 7, 2007.
Torok, Michael et al; (2003) "Modulation of transendothelial permeability and expression of ATP-binding cassette transporters in cultured brain capillary endothelial cells by astrocytic factors and cell-culture conditions"; *Experimental Brain Research* 153(3)356-365.
Supplementary European Search Report for Application No. 06733164.5-2406, regional application of PCT/NZ2006000075 (corresponding to the present application) dated May 19, 2008.
Examination Report for AU 2006237681, a related Australian application, Aug. 25, 2010, 2 pp.
Office Action in related application, U.S. Appl. No. 12/210,696, Sep. 9, 2010, 14 pp.
Office Action in related application, U.S. Appl. No. 11/916,963, Sep. 20, 2010, 21 pp.
Written Opinion in related application, PCT/NZ2006/000141, Aug. 16, 2006, 3 pp.
International Preliminary Report on Patentability in related application, PCT/NZ2006/000141, Jun. 20, 2007, 5 pp.
Search Report in related application, PCT/NZ2006/000141, Aug. 16, 2006, 7 pp.
Written Opinion in related application, PCT/NZ2006/000075, Mar. 12, 2007, 4 pp.
International Preliminary Report on Patentability in related application, PCT/NZ2006/000075, May 21, 2007, 23 pp.
Search Report in related application, PCT/NZ2006/000075, Jun. 27, 2006, 3 pp.
Emerich et al. (2005) "The Choroid Plexus in the Rise, Fall and Repair of the Brain," *Bioassays* 27:262-274.
Gorba et al. (2006) "Neural Regeneration Protein is a Novel Chemoattractive and Neuronal Survival-Promoting Factor," *Exp. Cell Res.* 312:3060-3074.

(Continued)

*Primary Examiner* — Jim Ketter
(74) *Attorney, Agent, or Firm* — Greenlee Sullivan P.C.

(57) ABSTRACT

The present invention is directed to the use of choroid plexus cells and/or choroid plexus conditioned media for enhancing the growth, survival and/or maintenance of function of non-choroid plexus cells grown in long term or short term culture.

19 Claims, 3 Drawing Sheets

OTHER PUBLICATIONS

Harrison, L.C. (2006) "Prevention of Autoimmune Disease: Type 1 Diabetes as a Paradigm", The Autoimmune Diseases, Chapter 75, 1045-1062.

Ramiya and Maclaren (1996) "Immunotherapies in Diabetes", TEM 7(7)252-257.

Reimann et al. (2009) "An update on preventive and regenerative therapies in diabetes mellitus", Pharmacology & Therapeutics 121:317-331.

Wherrett and Daneman (2009) "Prevention of Type 1 Diabetes", Endocrinology & Metabolism Clinics of North America, 38(4):777-790.

Yu and Eisenbarth (2006) "Mechanisms underlying type I diabetes and islet transplantation" Drug Discovery Today: Disease Mechanisms 3(2):155-162.

* cited by examiner

BR 50 - Day 60

CHOROID PLEXUS PREPARATION AND USES THEREOF

FIELD OF THE INVENTION

The present invention relates to the field of cell culture media and to methods for culturing cells in vitro or ex-vivo. The present invention has applications in the areas of cell culture and tissue transplantation.

BACKGROUND OF THE INVENTION

In order to successfully culture cells in vitro or ex-vivo, the cell culture media must comprise all of the nutrients required for sustainable cell growth and proliferation including sugars, amino acids, vitamins, salts, and in some cases trace metal ions, purines, and pyrimidines. These media are also often supplemented with animal serum.

Serum is usually derived from either foetal calf, newborn calf or horse and added to cell culture media in concentrations from 0.5 to 20% v/v. In addition to supplying growth enhancing components, serum also functions as a carrier/buffer/chelator for labile or water insoluble molecules, as well as a toxin neutraliser, protease inhibitor, cell attachment enhancer and as a protective agent in agitated suspension cultures.

The use of serum in cell culture media, however, has several disadvantages. It is comparatively expensive, it is not a defined component, and different lots of serum may vary in the concentration of compounds present and thus result in unpredictable culture growth and productivity. Serum may also be the source of contaminants such as mycoplasma, bacteriophages, viruses and toxins. Additionally, the protein in serum may complicate the purification of cell products from cell culture media.

In efforts to overcome the disadvantages of serum containing medium, serum-free media have been developed in which serum is substituted with better defined or more characterised components. Due to the complexity of serum and the different growth requirements of different types of cells, this has resulted in a variety of different media compositions. In most such serum-free media the serum is substituted by "cocktails" of trace elements, lipids, hormones, growth factors as well as purified proteins. Unfortunately, such purified proteins, such as human serum albumin, possess many of the disadvantages of serum. For example, human serum albumin is expensive and periodically scarce, and different sources may vary in the concentration of compounds present and therefore result in unpredictable culture growth and productivity. Serum albumin may also be the source of unknown contaminants including viruses. Both serum and serum albumin are also a major source of undefined differentiation factors which prevent the controlled growth and differentiation of specific cell types in culture.

The use of "feeder cells" in some cell culture systems has been developed to enhance the culture medium by releasing (or absorbing) components into (or from) it. Such "feeder cells" usually consist of adherent growth arrested but viable and bioactive cells that are used as a substratum on which other cells are grown in a co-culture system. Conditioned media (or cell-free culture supernatant) may also be used to supplement normal cell culture media as it contains numerous (undefined) mediator substances (including cytokines and growth factors) that were released into it by cells which were previously cultured therein.

Serum and serum albumin-free culture media are mainly available for specific cell types, such as stem cells. Feeder cells and conditioned media are also targeted towards fastidious cells and cell lines, such as embryonic stem cells.

It would be desirable to provide a cell culture media which is useful for supporting the growth and functionality of a wide variety of cell types grown in culture including cells and tissues grown ex-vivo and in vitro for both short periods and for extended periods of time. It is an object of the present invention to go some way towards achieving this desideratum and/or to provide the public with a useful choice.

SUMMARY OF THE INVENTION

The present invention is directed to the use of choroid plexus (CP) cells and/or CP conditioned media for enhancing the growth, survival and/or maintenance of function of non-CP cells grown in long term or short term culture.

CP conditioned media is known to improve the growth rate of SKs (neuroblastoma) cells in vitro and to increase the rate of dopamine uptake in mesencephalon cells in vitro (WO 00/66188). However, it is not known if such CP conditioned media is useful as a "general" cell culture media for enhancing the growth, survival and/or maintenance of function of a variety of non-CP cells in long term or short term culture.

In addition, as CP cells do not necessarily grow in sheets or layers in culture, it was not known whether CP cells could be co-cultured with non-CP cells to act as a "feeder" cell population to enhance the growth, survival and/or maintenance of function of non-CP cells in long term or short term culture.

The present inventors have surprisingly found that a CP preparation, comprising CP cells or CP conditioned media, is useful for enhancing the growth, survival and/or maintenance of function of non-CP cells in long term or short term culture.

It has also been surprisingly found that CP cells or CP conditioned media is useful for protecting non-CP cells in culture from serum deprivation-induced cell death.

According to the present invention there is provided a use of CP cells and/or CP conditioned media in the manufacture of a CP preparation for enhancing the growth, survival and/or maintenance of function of non-CP cells in long term or short term culture, wherein the CP preparation comprises:
 a) a CP cell population capable of producing one or more factors that support the survival and growth of non-CP cells; and/or
 b) a CP cell culture capable of producing one or more factors that support the survival and growth of non-CP cells; and/or
 c) CP conditioned media from a) or b) containing one or more factors that support the survival and growth of non-CP cells.

The non-CP cells may be neuronal or non-neuronal cells selected from the group comprising primary corticoid neuronal cells, islet β-cells, cells capable of producing or secreting factor VIII, cells capable of producing factor VIII and Von Willebrand factor, cardiac myocytes, cells of the conducting system of the heart such as the sinus node, atrioventricular nodal cells and the bundle of His, and cells involved in the repair of malformations in the newborn.

Preferably, the non-CP cells are cultured for a short term prior to transplantation into a recipient. For example, islet β-cells may be cultured according to the present invention prior to implantation into a recipient in the treatment of diabetes.

The non-CP cells may comprise cells obtained from a different species to the cells of the CP preparation. Thus, the present invention may be useful for enhancing the growth and survival of non-CP cells that are to be used in xenotransplantation.

The non-CP cells may be in a quiescent state before being cultured with the CP preparation of the present invention, such as freeze dried or frozen.

The one or more factors capable of supporting the survival and growth of non-CP cells may comprise neurotrophins, growth factors, trophic factors, cytokines, mitogens, matrix cell support factors, proteases capable of degrading toxic protein precipitates (such as amyloid and huntingtin), and proteins capable of complexing toxic metal ions (such as transferrin and ceruloplasmin).

The CP cells of a) and/or b) may comprise a purified population of CP cells or they may additionally or alternatively comprise CP-derived cells selected from the group comprising glial or glial-derived cells, epithelial cells, multipotent neuronal precursor cells, progenitor cells, and cells positive for neuronal precursor cell markers (such as neu-N).

The CP cells may be obtained directly from a suitable mammalian donor or may be obtained from a primary or secondary CP cell culture or from a CP cell line including an immortalised CP cell line, or from a combination of any of the above sources. The CP cells in culture may have been genetically modified. The CP cells obtained directly from a donor, may comprise cerebro spinal fluid containing one or more CP cells.

The CP and/or non-CP cells may comprise isolated cells or clusters of cells and may be "naked" or encapsulated, for example, in alginate. Where the CP and non-CP cells are "naked", they may be "free" to make direct contact with one another or they may be separated by a biocompatible separation means which allows the diffusion of secreted factors from the CP cells to the non-CP cells. The encapsulation of the CP and/or non-CP cells may function as such a biocompatible separation means.

The non-CP cells are preferably non-neuronal cells and the invention preferably provides a use of CP cells and/or CP conditioned media in the manufacture of a CP preparation for enhancing the growth, survival and/or maintenance of function of non-neuronal cells in long term or short term culture, wherein the CP preparation comprises:
  a) a CP cell population capable of producing one or more factors that support the survival and growth of non-neuronal cells; and/or
  b) a CP cell culture capable of producing one or more factors that support the survival and growth of non-neuronal cells; and/or
  c) CP conditioned media from a) or b) containing one or more factors that support the survival and growth of non-neuronal cells.

The present invention further provides a method of enhancing the growth, survival and/or maintenance of function of non-CP cells in long term or short term culture, comprising the step of incubating non-CP cells with a CP preparation comprising:
  a) a CP cell population capable of producing one or more factors that support the survival and growth of non-CP cells; and/or
  b) a CP cell culture capable of producing one or more factors that support the survival and growth of non-CP cells; and/or
  c) CP conditioned media from a) or b) containing one or more factors that support the survival and growth of non-CP cells.
Preferably the non-CP cells are non-neuronal cells.

The present invention also provides a method of protecting non-CP cells in culture from serum deprivation-induced cell death comprising the step of incubating non-CP cells in a serum free media with a CP preparation comprising:
  a) a CP cell population capable of producing one or more factors that support the survival and growth of non-CP cells; and/or
  b) a CP cell culture capable of producing one or more factors that support the survival and growth of non-CP cells; and/or
  c) CP conditioned media from a) or b) containing one or more factors that support the survival and growth of non-CP cells.
Preferably the non-CP cells are non-neuronal cells.

The present invention is also directed to the non-CP cells cultured using the CP preparation of the present invention.

The term "comprising" as used in this specification and claims means "consisting at least in part of", that is to say when interpreting independent claims including that term, the features prefaced by that term in each claim all need to be present but other features can also be present.

BRIEF DESCRIPTION OF THE FIGURES

The invention will now be described in more detail with respect to the figures of the accompanying drawings in which.

DETAILED DESCRIPTION OF THE INVENTION

Figure 1:
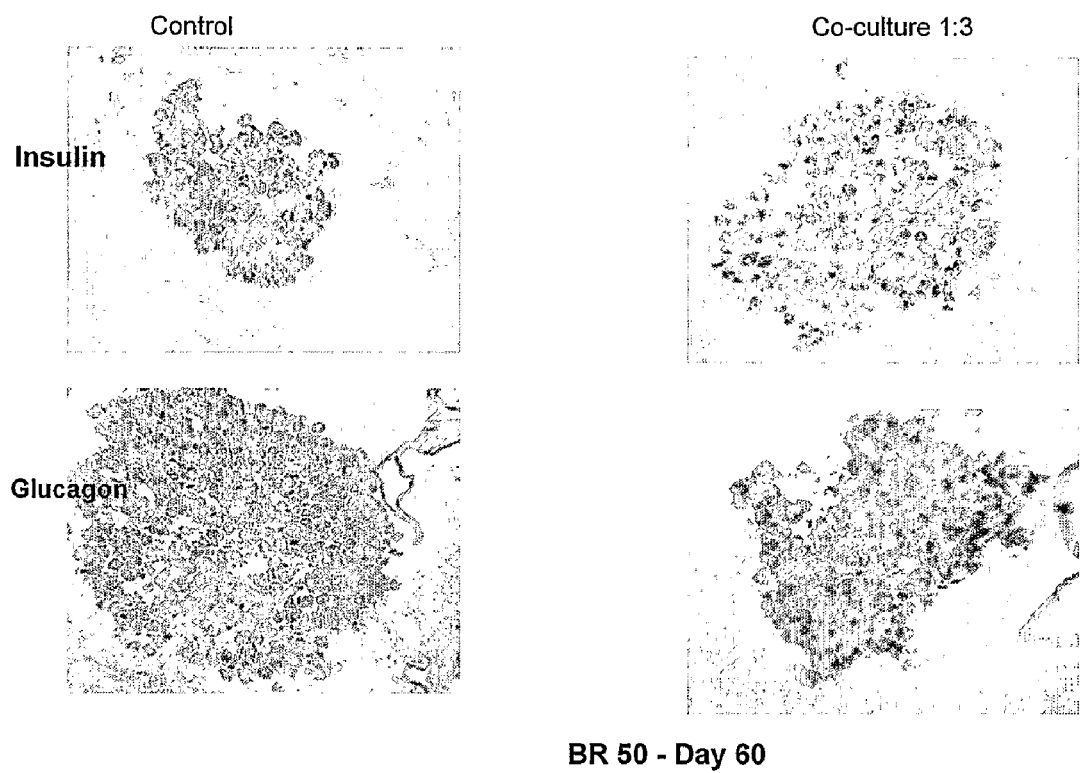
FIG. 1 shows in a series of photomicrographs, the immunoperoxidase staining of islet cells grown in the absence of choroid plexus cells (Control), or in co-culture with choroid plexus cells at a ratio of 1:3(1:3). Cells stained for insulin are presented on the top row, while cells stained for glucagon are presented on the bottom row. These photomicrographs show that CP cell preparations enhance insulin and glucagon production in the islet.

The present invention is directed to the use of CP cells and/or CP conditioned media for enhancing the growth, survival and/or maintenance of function of non-CP cells in long term or short term culture.

The CP are lobulated structures comprising a single continuous layer of cells derived from the ependymal layer of the cerebral ventricles. One function of the choroid plexus is the secretion of cerebrospinal fluid (CSF). Cerebrospinal fluid fills the four ventricles of the brain and circulates around the spinal cord and over the convexity of the brain. The CSF is continuous with the brain interstitial (extracellular) fluid, and solutes, including macromolecules, are exchanged freely between CSF and interstitial fluid. In addition to the production of CSF, the choroid plexus has been associated with the formation of the CSF-blood barrier (Aleshire S L et al., "Choroid plexus as a barrier to immunoglobulin delivery into cerebrospinal fluid." J Neurosurg. 63:593-7, 1985). However, its broader function is the establishment and maintenance of baseline levels of the extracellular milleu throughout the brain and spinal cord, in part by secreting a wide range of growth factors into the CSF. Studies have reported the presence of numerous potent trophic factors within choroid plexus including TGFb, GDF-15, GDNF, IGF2, NGF, NT-3, NT-4, BDNF, VEGF, and FGF2 (for review see Johanson C E et al., "Choroid plexus recovery after transient forebrain ischemia: role of growth factors and other repair mechanisms." Cell Mol Neurobiol. 20:197-216, 2000).

The present invention recognises that choroid plexus (CP) cells are capable of secreting factors, such as neurotrophins, growth factors, vascular endothelial growth factor, trophic factors, cytokines, mitogens, matrix cell support factors, enzymes such as proteases, alpha-1 antitrypsin, amylase, lipase, sucrase, lactase or maltase and other proteins which may be useful in enhancing the growth, survival and maintenance of function of non-CP cells in long term or short term culture.

Specifically, the present invention provides a use of a CP preparation for enhancing the growth, survival and maintenance of function of non-CP cells in long term or short term culture, wherein the preparation comprises:

a) a CP cell population capable of producing one or more factors that support the survival and growth of non-CP cells; and/or b) a CP cell culture capable of producing one or more factors that support the survival and growth of non-CP cells; and/or c) CP conditioned media from a) or b) containing one or more factors that support the survival and growth of non-CP cells.

The non-CP cells may be neuronal or non-neuronal cells selected from the group comprising primary cortical neuronal cells; islet β-cells; fibroblasts; cells capable of producing or secreting factor VIII such as hepatocytes, gall bladder epithelial cells, gall bladder endothelial cells, bile duct epithelial cells, bile duct endothelial cells, hepatic vessel epithelial cells, hepatic vessel endothelial cells, sinusoid cells, non-parenchymal liver cells and umbilical cord endothelial cells; cells capable of producing Factor VIII and Von Willebrand factor such as endothelial cells, hepatic endothelial cells and umbilical cord endothelial cells; cardiac myocytes; cells of the conducting system of the heart such as the sinus node, atrioventricular nodal cells and the bundle of His; and cells involved in the repair of malformations in the newborn and inborn errors of metabolism such as aminoacidopathies, organic acidurias, inherited specific protein deficiencies, enzymopathies including urea cycle disorders, disorders of pigment metabolism, disorders of purine metabolism and disorders of polysaccharide and muco-polysaccharide and glycoprotein metabolism.

The non-CP cells which are to be cultured, may be in a quiescent state, such as freeze dried or frozen, before being cultured with the CP preparation defined herein. Such quiescent cells will be cultured in a suitable cell culture medium, such as Hams F-12, Dulbecco's modified Eagles medium (DME), RPM1 1640, and Iscove's modified DME, under suitable conditions depending on the cell type, as would be appreciated by a skilled worker. The CP preparation is then added to the non-CP cells in culture in an amount that will enhance the growth, survival and/or maintenance of function of the non-CP cells, when compared with such cells to which the CP preparation has not been added.

The CP preparation may comprise a purified population of CP cells and/or CP-derived cells selected from glial or glial derived cells, epithelial cells, multipotent neuronal precursor cells, progenitor cells and cells positive for neuronal precursor cell markers (such as neu-N).

The CP and CP-derived cells of the CP preparation may be obtained from any donor mammal, including pigs, sheep, cows, goats, rabbits, mice and primates, including rhesus monkeys and humans, using methods known in the art for example as described in WO 00/66188. The CP and CP-derived cells may be obtained directly from the brain of the donor or from the cerebrospinal fluid.

Alternatively, CP and CP-derived cells of the CP preparation may be obtained from a CP or CP-derived cell line, including an immortalized cell line, such as TR-CSFB cells (Hosoya K, Hori S, Ohtsuki S, Terasaki T, (2004). A new in vitro model for blood-cerebrospinal fluid barrier transport studies: an immortalized choroid plexus epithelial cell line derived from the tsA58 SV40 large T-antigen gene transgenic rat. Adv Drug Deliv Rev. 56(12):1875-85); or Z310 cells (Zheng W, Zhao Q, (2002), Establishment and characterization of an immortalized Z310 choroidal epithelial cell line from murine choroid plexus. Brain Res. 958(2):371-80).

The CP and CP-derived cells of the CP preparation may be genetically modified to produce one or more desired factors which will enhance the survival and growth of a non-CP cell in long term or short term culture, using genetic modification techniques which are well known in the art.

The CP preparation may be freeze dried or frozen for storage prior to use in the present invention as would be appreciated by a skilled worker. Upon use, the frozen or freeze dried CP preparation may be simply reconstituted.

The CP preparation may comprise isolated CP and/or CP-derived cells or small clusters of such cells which may be "naked", i.e. in their natural state after harvesting from a donor or cell culture, or they may be encapsulated in a biocompatible material such as alginate by methods known in the art (see for example WO 00/66188 and U.S. Pat. No. 6,322, 804). Alternatively, such cells, either naked or encapsulated, may be placed in a confinement means, which acts to separate the CP preparation from the non-CP cells in culture, such as a tube or other structure made of biocompatible material which will allow the diffusion of growth factor etc, from the CP preparation to the non-CP cells in culture.

Alternatively, the CP preparation comprises conditioned media from CP and/or CP-derived cells. Conditioned media is prepared from a CP and/or CP-derived cell culture in which the cells have been cultured for a period of time and under conditions that allow secretion of the growth factors etc, from the CP and/or CP-derived cells into the media. The conditioned media is then separated from the cells to provide a factor rich, cell-free CP preparation for use in the invention.

The CP preparation defined herein is useful for culturing non-CP cells for a short term or a long term. As mentioned above, non-CP cells may be cultured in the short term prior to transplantation into a recipient. When non-CP cells are to be cultured over a long period of time, such as for example, in a continuous culture system, the CP preparation may be maintained separately from the non-CP cell culture and added thereto by way of an infusion device or the like, either manually or automatically, as and when required.

The CP preparation may alternatively be embedded in a polymer or other biocompatible matrix, which may be degradable when in contact with the non-CP cells in culture, to release the CP cells. Alternatively, the polymer may be non-degradable, but instead may be permeable to the growth factor etc secreted or released from the CP preparation.

The invention also contemplates the use of cerebrospinal fluid (CSF) as the CP preparation for use in the present invention. As discussed above, CP cells in vivo secrete growth factors etc into the CSF. Thus, CSF will contain CP secreted factors capable of enhancing growth and survival of non-CP cells and may be useful in the present invention. The CSF may comprise CP and/or CP-derived cells.

The present invention is also directed to a method of enhancing the growth, survival and/or maintenance of function of non-CP cells in long term or short term culture, comprising the step of incubating non-CP cells with a CP preparation comprising:
  a) a CP cell population capable of producing one or more factors that support the survival and growth of non-CP cells; and/or
  b) a CP cell culture capable of producing one or more factors that support the survival and growth of non-CP cells; and/or
  c) CP conditioned media from a) or b) containing one or more factors that support the survival and growth of non-CP cells.

The present invention is further directed to a method for protecting non-CP cells in culture from serum deprivation-induced cell death comprising the step of incubating non-CP cells in a serum free media with a CP preparation comprising:
  a) a CP cell population capable of producing one or more factors that support the survival and growth of non-CP cells; and/or
  b) a CP cell culture capable of producing one or more factors that support the survival and growth of non-CP cells; and/or
  c) CP conditioned media from a) or b) containing one or more factors that support the survival and growth of non-CP cells.

Preferably the non-CP cells are non-neuronal cells.

There are many benefits of the present invention including:
  protection against damage to non-CP cells in culture from events such as injury, disease, trauma, serum-deprivation;
  prevention or minimisation of apoptotic cell death of non-CP cells in culture;
  regeneration of damaged cells of non-CP cells in culture;
  impeding or stopping cell death and/or cell death cascades resulting from events such as cell injury, disease, trauma, serum-deprivation of non-CP cells in culture;
  enhancement of cell function of non-CP cells in culture;
  enhancement of cell survival of non-CP cells in culture;
  provision of factors necessary for cell survival, growth and/or maintenance of function of non-CP cells in culture.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

EXAMPLE 1

Use of a Cp Preparation to Support Growth and Survival Of Non-neuronal Cells in Culture Free and encapsulated pig islet cells were co-cultured with CP cells or CP conditioned media and the viability, maturation and function of the islet cells were assayed under short term and long term culture conditions.

Materials and Methods
Isolation and Purification of Islet Cells

Porcine islet cells were isolated by collagenase (Liberase) digestion of the minced pancreas via the procedure documented by Ricordi et al. (1990), with some modifications. Using aseptic technique, the glands are distended with Liberase (1.5 mg/ml), trimmed of excess fat, vessels and connective tissue, minced and digested at 37° C. in a shaking water bath for 10 minutes at 120 rpm. Following digestion, the cells were passed through a sterile 280 µm mesh into a sterile beaker. A second digestion (10 min) was used for any undigested tissue.

Further details on the collagenase digestion procedure are available in Diatranz's Manual of Standard Operating Procedures, SOP P101 and also in previous patents, such as for example, WO 01/52871 and WO 02/32437.

Islet Yield and Viability

The islet yield was determined via dithizone (DTZ) staining of the cells. Dithizone is a zinc-chelating agent that selectively stains zinc in the islets of Langherhans, producing a distinctive red appearance.

The viability of the islet cells was determined using acridine orange and propidium iodide (AO/PI). Acridine orange is a fluorescent stain that readily passes through all cell membranes to stain the cytoplasm and nucleus. Bright green fluorescence in both the nucleus and cytoplasm on exposure to ultraviolet (UV) light denotes intact live cells. Conversely, propidium iodide is a fluorescent stain that cannot pass through an intact membrane. It emits a bright red fluorescence when exposed to UV light, and the presence of propidium iodide in a cell nucleus indicates severe damage or a dead cell.

Islet Maturation and Function: In vitro Insulin Secretory Capacity

Static glucose stimulation (SGS) was used to assess the in vitro function of the porcine islets by exposing them to both low concentrations of glucose (2.8 mmol/L) and high concentrations of glucose (19.4 mmol/L) plus theophylline (10 mmol/L). The insulin stimulation index was then calculated as the ratio of insulin released from the islets (in µU/100 IEQ/hour) for the high versus low concentrations of glucose in the SGS test. An insulin stimulation index >3 is considered an acceptable indicator of viable cells.

Histology

After SGS the cells were placed in a thrombin clot (20-50 ul of porcine plasma mixed with same amount of Thrombin 1000 U/ml). The clot with cells was then fixed in 10% formalin and embedded in paraffin wax. 5 µm sections were prepared for standard Haematoxylin and Eosin (H&E), insulin and glucagon (IPX) immunoperoxidase staining.

Co-Culture Conditions

Islet preparations from a single batch (BR50) were co-cultured with preparations of CP cells or media from CP cell cultures as follows:
1. Porcine Free Islets in co-culture with Encapsulated CP (ratio 1:1). The two cell types were separated by a 40 µm mesh membrane with free islets in a basket insert and choroid plexus microcapsules free floating in the well below the insert. All experiments were carried out in triplicate.

2. Porcine Free Islets in Aggregates with Free CP (ratio 1:1). Islets and choroid plexus cells aggregates were put together on day 3 after isolation. The purpose of the aggregates was to restore Schwann cells around the islets.

3. Porcine Free Islets cultured with CP conditioned medium. The free islets were placed in a 40 μm mesh basket insert, in 6 well plates. The CP conditioned media was the supernatant from 48-72 hr culture supernatants of CP cell cultures (batch BR52).

4. Encapsulated Porcine Islets cultured with Free CP cell clusters (ratio 1:3). The encapsulated islets were contained in a 40 μm mesh basket insert and the CP cells were attached to the 6 well plate.

5. Encapsulated Porcine Islets cultured with CP conditioned media. The encapsulated islets were contained in a 40 μm mesh basket insert and the CP cells were attached to the 6 well plate.

Results

1. Porcine Free Islets in co-culture with Encapsulated CP Cells (ratio 1:1)

Porcine Islets co-cultured with encapsulated CP cells remained alive and responded to static glucose stimulation (SGS) for up to 21 days. Insulin response increased 59.8% at day 21 compared to day 7 as shown in Table 1, below.

Histology showed insulin and glucagon positive cells (IPX) at day 21.

TABLE 1

| Day | Condition | Basal | Max response | Basal |
|---|---|---|---|---|
| d7 | Free Islets control | 7.8 | 30.0 | 3.6 |
| d7 | Free Islets co-cultured with encapsulated CP ratio 1:1 | 30.8 | 193.1 | 17.1 |
| d21 | Free Islets control | 23.3 | 121.1 | 24.7 |
| d21 | Free Islets co-cultured with encapsulated CP ratio 1:1 | 61.3 | 308.6 | 41.9 |

2. Porcine Free Islets in Aggregates with Free CP cells (ratio 1:1)

The islets released good amounts of insulin up to day 60. Insulin production was increased by a maximum of 83% on day 21. The response at day 60 was similar to day 7 as shown in Table 2, below.

TABLE 2

| Day | Condition | Basal | Max response | Basal |
|---|---|---|---|---|
| D7 | Free Islets control | 7.8 | 30.0 | 3.6 |
| D7 | Free Islets in aggregates with CP | 28.8 | 211.5 | 15.9 |
| D21 | Free Islets control | 23.3 | 121.1 | 24.7 |
| D21 | Free Islets in aggregates with CP | 46.3 | 388.5 | 44.7 |
| D60 | Free islets control | | No viable islets | |
| D60 | Free Islets in aggregates with CP | 31.5 | 204.3 | 28.0 |

3. Free Islets Cultured with CP Conditioned Medium

The islets produced large amounts of insulin in the presence of CP conditioned media. For example, at day 7 insulin was increased by 332% compared to the control islets and 114% at day 21. At day 60, the islets produced 612% more insulin compared to the control cells as shown in Table 3, below.

TABLE 3

Free Islets cultured with CP conditioned media

| Day | Basal | Max response | Basal |
|---|---|---|---|
| d7 control | 0.8 | 49.2 | 2.3 |
| d7 CP media | 12.2 | 213.0 | 5.8 |
| d21 control | 44.2 | 317.1 | 10.6 |
| d21 CP media | 85.0 | 677.7 | 33.3 |
| d60 control | 135.3 | 79.2 | 5.9 |
| d60 CP media | 113.6 | 563.7 | 36.8 |

4. Encapsulated Porcine Islets Cultured with Free CP Cell Clusters (Ratio 1:3)

Compared with the control, the response to SGS, after 21 days in culture, was superior following co-culture with CP cell clusters as shown below in Table 4.

TABLE 4

Encapsulated Porcine Islets cultured with CP cell clusters (ratio 1:3)

| Day | Basal | Max response | Basal |
|---|---|---|---|
| D7 control | 0.7 | 27.0 | 1.0 |
| d7 CP clusters | 0.4 | 17.9 | 0.3 |
| d21 control | 11.9 | 94.7 | 4.6 |
| d21 CP clusters | 6.4 | 115.7 | 4.0 |

The histology of these Islet cells was also investigated after 60 days of culture.

The co-cultured Islet cells at day 60 showed formation of new clusters of insulin positive cells and more mature Islets compared to the control Islets, (top row, FIG. 1), as well as a greater number of glucagon positive cells, (including strongly positive cells) when compared to the control cells (bottom row, FIG. 1).

5. Encapsulated Porcine Islets Cultured with CP Media

The response of the Islets to SGS was 368% higher than the control cells on day 7; 350% higher than the control cells at day 21, and at day 60 the amount of insulin went up to 173% compared to day 21 results as shown in Table 5, below.

TABLE 5

Encapsulated Porcine Islets cultured with Choroid Plexus media

| Day | Basal | Max response | Basal |
|---|---|---|---|
| d7 control | 0.7 | 27.0 | 1.0 |
| d7 CP media | 5.0 | 126.4 | 3.5 |
| d21 control | 11.9 | 94.7 | 4.6 |
| d21 CP media | 65.1 | 426.4 | 16.5 |
| d60 CP media | 222.5 | 1167.4 | 80.8 |

Summary

These data indicate that CP preparation enhance the survival and function of insulin-producing islet cells.

EXAMPLE 2

CP Preparation Protects Neuronal Cells From Serum Deprivation-induced Cell Death in Culture Choroid plexus (CP) cells secrete a cocktail of neurotrophic factors. In the following study, CP conditioned media promoted the survival and function of fetal rat neuronal cells in culture, providing protection from neurotrophic deprivation in vitro.

Materials and Methods
In vitro Biological Activity

In vitro biological activity of choroid plexus was determined by placing CP-conditioned media onto primary day 15 embryonic cortical neurons and measuring its effects on neuronal survival under serum deprivation conditions. The techniques used for preparing and maintaining primary cortical neuronal cultures were similar to those described previously (Fukuda A, Deshpande S B, Shimano Y, Nishino H. "Astrocytes are more vulnerable than neurons to cellular Ca2+ overload induced by a mitochondrial toxin, 3-nitropropionic acid." Neuroscience. 87:497-507, 1998.). Brains were removed from Wistar rats on embryonic day 15 and incubated in HBSS chilled on ice. The cortical tissues were dissected free, chopped into small pieces and incubated with $Ca^{2+}$-free Hanks' solution containing trypsin (0.05 mg/ml) and collagenase (0.01 mg/ml) at 37° C. for 30 minutes, followed by the addition of soybean trypsin inhibitor (0.1 mg/ml) and DNase (0.1 mg/ml). The tissue was then centrifuged for 5 minutes (1000 rpm) in Dulbecco's modified Eagle's medium supplemented with 10% fetal bovine serum. The pellet was re-suspended and a homogenous cell suspension was made by gentle trituration using a fire-polished Pasteur pipette. Cells were plated on 35 mm tissue culture dishes ($5 \times 10^4$ cells/ml). The culture dishes were kept in a humidified incubator under 5% $CO_2$ and 95% air at 37° C. for 4 days. On day 4, cells were re-plated in 24-well plates, and over the next two days, a subset of cells were cultured without serum and with a range of concentrations of conditioned media (0-30%). CP-conditioned media was prepared as described in Example 3 herein, and stored at −20° C. prior to use. On day 6, cell viability was analyzed using Trypan blue exclusion. All studies were conducted in triplicate.

Neuronal Cell Function

Primary cultures of day 15 fetal rat brain were prepared according to the method described above, and placed in 96-well plates. The cultures were established for 4 days with Neurobasal medium supplemented with B27 nutrients and with fetal bovine serum (10%). After establishment, the cultured cells were divided into three groups: control cells grown in serum-supplemented media; cells grown in unsupplemented media; and cells grown in media supplemented with CP-conditioned media. The number of neurite processes and the degree of outgrowth of the neurite processes was then determined for each group of cells, as indicators of neuronal cell function.

Results
In vitro Biological Activity

Figure 2:
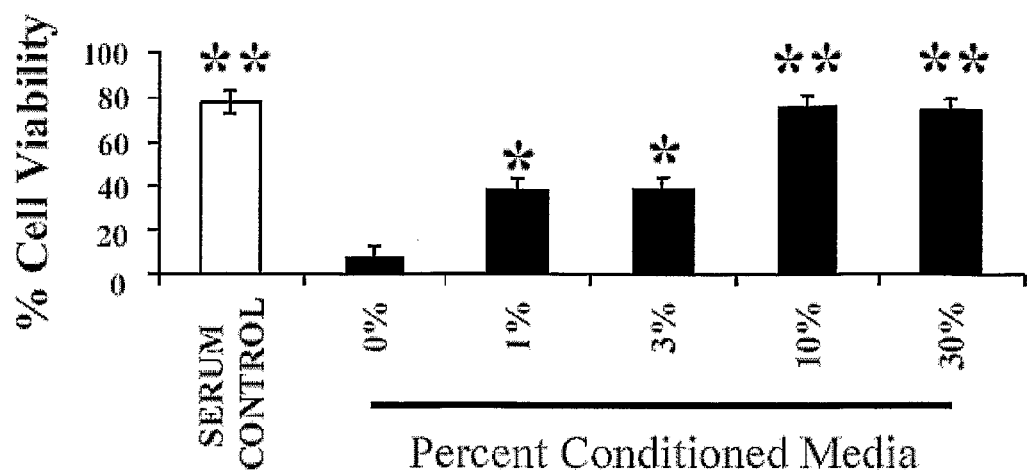
FIG. 2 shows conditioned media (CM) from CP preparations enhances neuronal viability. The effect of serum-free CM at different concentrations from cultured choroids plexus on neuronal cell viability, wherein *=P<0.0001 for 10% and 30% versus 0%; **=P<0.0001 versus 0%, 1% and 3% is shown.

In vitro tests demonstrated that molecules secreted from the encapsulated choroid plexus exerted potent neurotrophic effects. An overall ANOVA revealed treatment effects on neuronal cell viability (ANOVA, $F_{5,38}=109.01$, $p<0.0001$). Primary cortical neurons deprived of serum for 2 days exhibited significant cell death (approximately 90%) compared to cells maintained in serum media (FIG. 2). Conditioned media collected from pig choroid plexus significantly protected against serum deprivation-induced cell death. This effect was dose-dependent with maximal effects obtained when serum-deprived neurons were cultured with 10% to 30% conditioned media from pig choroid plexus ($p$'s<0.0001). At these concentrations, neuronal survival was 60%-85% and did not differ significantly from serum maintained cells ($p$'s>0.05).

Neuronal Cell Function

Neurons cultured in Neurobasal medium supplemented with B27 nutrients and with fetal bovine serum (10%) become established and put out neurite extensions which comprise the principle and essential components of neuronal networking. These neurite processes increased in number and in length under the influence of neurotrophic growth factor present in serum.

Figure 3:
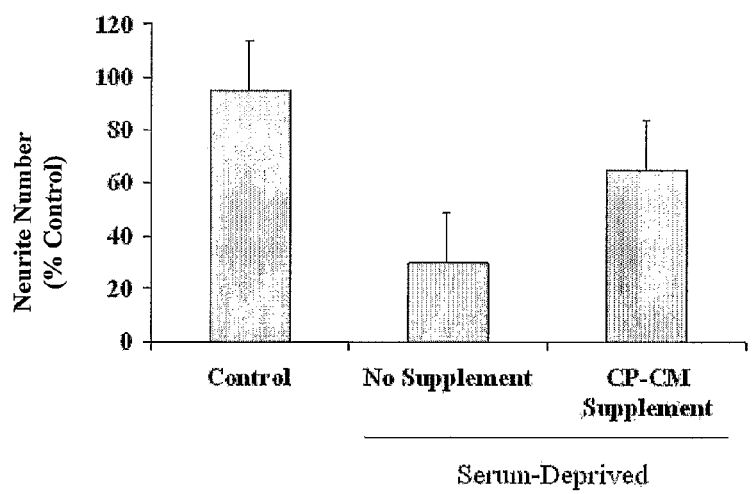
FIG. 3 shows the effect of conditioned media from cultured choroid plexus on the number of neurite processes in neuronal cell cultured in media supplemented with fetal bovine serum (Control), unsupplemented media (No Supplement), and in media supplemented with choroid plexus conditioned media (CP-CM Supplement), whereby CP conditioned media increases the numbers of neuritis on neuronal cells.
Figure 4:
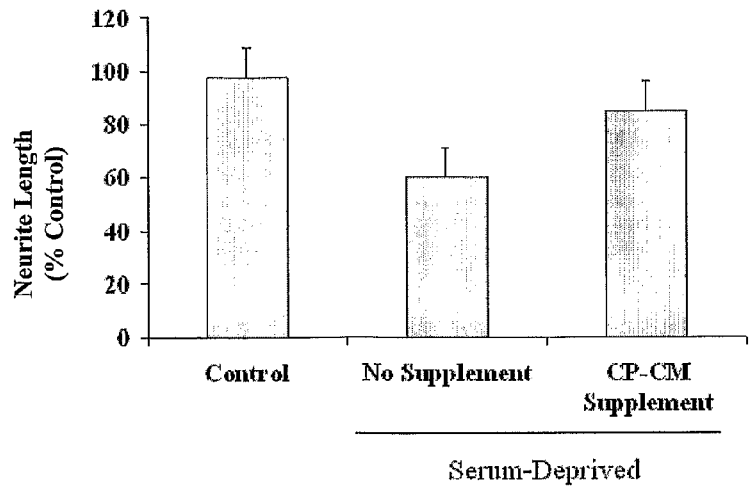
FIG. 4 shows the effect of conditioned media from cultured choroid plexus on the length of outgrowth of neurite processes in neuronal cell cultured in media supplemented with fetal bovine serum (Control), unsupplemented media (No Supplement), and in media supplemented with choroid plexus conditioned media (CP-CM Supplement), whereby CP conditioned media increases the length of neuritis on the neuronal cell.

Replacement of the media with unsupplemented media (so that the neurons were without the support of serum derived neurotrophic growth factors), resulted in a decrease in the number and length of neurites. Supplemention of the unsupplemented media by 50% with medium conditioned for 48 h by the secretory activity of CP cell clusters, resulted in the restoration of neurite numbers (CP-CM supplement, FIG. 3) and neurite extensions (CP-CM Supplement, FIG. 4) toward the numbers and length seen with 10% fetal bovine serum (FIGS. 3 and 4, Control).

EXAMPLE 3

CP Preparation Contains Multipotent Neuronal Cells Precursors

Choroid plexus (CP) cell clusters prepared according to the methods described herein contain cells that have the characteristics of multipotent neuronal precursors.

Materials and Methods
Cell Culture

Neonatal porcine and adult rat choroid plexus were isolated as described herein, and grown in cell culture with 5% $CO_2$ in air and RPMI supplemented with 2% neonatal porcine serum, nicotinamide and cyproxin as described in Example 1.

Immunohistochemistry

Cell clusters (approximately 2000-2500) were sedimented, media removed down to a volume of 100 microliters and the suspension mixed with 2% low-melting agarose in Hanks Balanced Salts solution (200 microliters) at 35-37 degrees C. The material was allowed to cool and the solidified agarose block containing the cell clusters was fixed in neutral buffered formalin. The block was processed using standard procedures into paraffin wax and sections of this block were cut (5 microns thick) on a microtome and placed on standard glass microscope slides. The sections were stained for neu-N using an anti-serum specific for neu-N using an immunohistochemical detection technique according to the anti-serum supplier's instructions.

Results

When tested after 7-8 days in culture, approximately 20% of the cells, mostly at the periphery of the clusters, were found to be positive for the neuronal precursor marker neu-N. These data indicate that choroid plexus comprise cells with the characteristics of multipotent neuronal precursors, and that such cells survive and maintain their phenotype when cultured under the conditions described herein.

Summary of Examples 2 and 3

These data indicate that CP preparation enhance the survival and functional differentiation of neuronal cells and can also produce multipotent neuronal precursors.

EXAMPLE 4

Pig Fibroblast Proliferation with Choroid Plexus (CP) Cells Conditioned Growth Media Serum free conditioned media from 24 hour cultures of CP cells were assessed for the capability to enhance the proliferation of fibroblasts.

Materials and Methods
CP Cells SFCM

Clusters of choroid plexus cells were grown in serum free conditioned media (SFCM) for 24 hours. The media were harvested, filtered and frozen to −80° C. till use.

Pig Skin Fibroblasts

Fibroblasts were derived from pig skin, cultured and passaged and frozen and thawed as required. Pig skin fibroblasts were seeded at 15,000 cells per well with FULL GROWTH MEDIA comprising Minimum Essential Media (MEM, Gibco, USA)+10% fetal bovine serum (FBS+0.08% Ciprofloxacin) in 1 ml cultures in triplicates in 24 well plates.

Pig skin fibroblasts were also seeded at 20,000 cells per well in SERUM FREE GROWTH MEDIA (MEM+0.08% Ciprofloxacin). Cells were seeded in 1 ml media in triplicates in 24 well plates and cell proliferation checked after 24 hours incubation.

Proliferation Assay

The proliferation of pig skin fibroblasts was assayed using the Cell Counting Kit-8 (CCK-8), Dojindo (Japan). The CCK-8 allows assays using Dojindo's tetrazolium salt, WST-8 (2-(2-methoxy-4-nitrophenyl)-3-(4-nitrophenyl)-5-(2,4-disulfophenyl)-2H-tetrazolium, monosodium salt), which produces a water-soluble formazan dye upon bioreduction in the presence of an electron carrier, 1-Methoxy PMS. CCK-8 solution is added directly to the cells. WST-8 is bioreduced by cellular dehydrogenases to an orange formazan product that is soluble in tissue culture medium. The amount of formazan produced is directly proportional to the number of living cells.

To cells seeded on 24 well plates, 100 ul CCK reagent was added to 1 ml growth media. The plate was incubated for 24 hours. 100 ul aliquots were transferred to 96 well plate and Optical Densities (ODs) were read against the control growth media with reagent (without cells) using an E-Liza MAT 3000 plate reader at 450 nm (DRG, USA).

The cell numbers were calculated from linear standard curves generated from ODs for a range of fibroblast cell numbers determined by haemocytometer and the CCK reagent.

Results

1. Pig Skin Fibroblasts in Full Growth Media and Serum Free Growth Media

Pig skin fibroblasts cultured in CP conditioned media resulted in an enhanced growth rate in both full growth media (Table 6) and serum free growth media (Table 7) compared to fibroblasts grown in the absence of CP conditioned media (control).

TABLE 6

| Media Conditions | Cell number Per Well | % |
|---|---|---|
| FULL GROWTH MEDIA (Control) | $159 \times 10^3$ | 100 |
| FULL GROWTH MEDIA + 5% CP cell SFCM | $183 \times 10^3$ | 115 |
| FULL GROWTH MEDIA + 10% CP cell SFCM | $178 \times 10^3$ | 112 |
| FULL GROWTH MEDIA + 15% CP cell SFCM | $190 \times 10^3$ | 120 |
| FULL GROWTH MEDIA + 20% CP cell SFCM | $173 \times 10^3$ | 109 |

TABLE 7

| Media Conditions | Cell number Per Well | % |
|---|---|---|
| FULL GROWTH MEDIA (Control) | $144 \times 10^3$ | 100 |
| FULL GROWTH MEDIA + 5% CP cell SFCM | $168 \times 10^3$ | 114 |
| FULL GROWTH MEDIA + 10% CP cell SFCM | $164 \times 10^3$ | 116 |
| FULL GROWTH MEDIA + 15% CP cell SFCM | $176 \times 10^3$ | 122 |
| FULL GROWTH MEDIA + 20% CP cell SFCM | $158 \times 10^3$ | 110 |

Summary

These data indicate that CP conditioned media contains factors that enhance the proliferation of non-neuronal cells such as fibroblasts.

EXAMPLE 5

Use of an Encapsulated CP Preparation to Enhance the Proliferation of Human Umbilical Vascular Endothelial Cells (HUVEC)

Materials and Methods

Isolation and Preparation of Encapsulated CP Cells

Choroid plexus was isolated from 7 day-old pigs as described herein. Following a 7-day incubation period in RMPI containing 2% neonatal porcine serum and antibiotics (RPMI-CP), acquired from the donor litter of piglets, choroid plexus clusters were encapsulated at a density of 30K/mL alginate in alginate-polyornithine-alginate microcapsules by known methods. Encapsulated choroid plexus (eCP) was allowed to incubate under optimal culture conditions for 3 days prior to co-culture with HUVEC. At this time, samples were assessed for secretion of vascular endothelial growth factor (VEGF) by incubating 6000 encapsulated cluster equivalents in 1 mL fresh RPMI-CP for 24 hours and measuring VEGF with a sandwich ELISA produced by R&D systems.

Co-culture of eCP with HUVEC

HUVEC cultures were established in 24-well tissue culture plates to 50% confluency in basal medium containing brain extract (BE), a formulation known to promote growth of HUVEC. The media was removed from all samples and fresh media and/or eCP was added to the wells. Each sample contained a total media volume of 1 mL. The groups were as follows:

TABLE 8

| Sample | N | Media |
|---|---|---|
| HUVEC | 10 | Basal + BE (Complete) |
| HUVEC | 10 | Basal (Incomplete) |
| eCP (2.5K) + HUVEC | 3 | Basal |
| eCP (5K) + HUVEC | 4 | Basal |
| eCP (10K) + HUVEC | 3 | Basal |

After 72 hours of co-culture, the eCP and conditioned media were collected, separated, and the media was assayed for VEGF over the 72 hour time course. HUVEC were counted by trypsinizing the cells and measuring DNA using the PicoQuant DNA assay kit from Molecular Probes following sonication to lyse the cells.

Results

Figure 5:
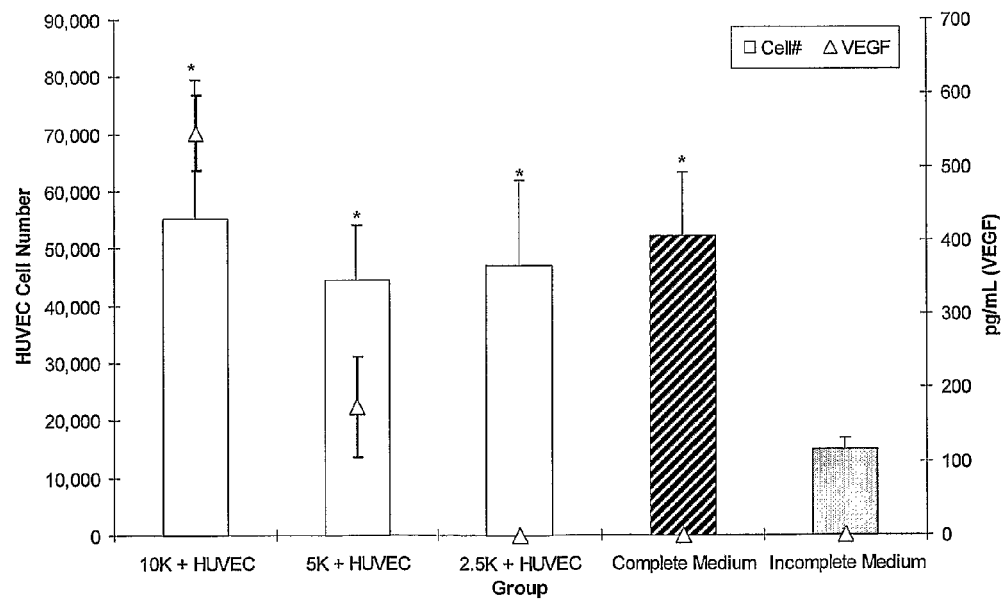
FIG. 5 shows the effect of a co-culture of encapsulated CP cells on the proliferation of human umbilical vascular endothelial cells (HUVEC) and on the secretion of VEGF into the culture media, whereby co-culture of encapsulated CP cells and HUVEC result in an increase in proliferation of HUVEC.

Conditioned medium from eCP held for 3 days in vitro showed that 6000 encapsulated clusters secreted 1.15±0.02 ng VEGF/1 mL/24 hours. When incubated with HUVEC in minimal medium, a distinct increase in cell proliferation of HUVEC was observed as seen in FIG. 5, which shows the cell number and final VEGF levels for each co-culture condition. The VEGF levels, shown on the right y-axis and corresponding to the triangle markers, were below the limit of detection for all groups except the 10K and 5K eCP groups which measured, respectively, 546±51 and 174±69 pg/mL/72 hours.

The cell counts shown in FIG. 5 demonstrates a clear effect of eCP on the proliferation of HUVEC that did not suggest a dose-dependence at the levels assessed in this experiment. All eCP groups and the group cultured in the media formulated specifically for HUVEC proliferation (complete medium) were statistically equivalent and higher than the cell count in the incomplete medium. The eCP groups, which lacked the brain extract formulated for HUVEC growth, elicited the same level of growth as the complete medium.

Summary

These results show that encapsulated choroid plexus secrete relatively high levels of bioactive VEGF. In a co-culture system with HUVEC, eCP was able to stimulate the same level of HUVEC growth in incomplete medium as the media containing brain extract specifically manufactured for HUVEC proliferation. This does not appear to be a dose dependent effect, however, due to the short half-life of VEGF in medium, the 72 hour duration of the experiment, and the unknown metabolic rate of the HUVEC, this possibility cannot be ruled out. These data indicate that eCP secrete factors that enhance the proliferation of non-neuronal cells such as umbilical cord cells.

Discussion

These experiments demonstrate that a CP preparation, comprising CP cells and/or CP derived cells and/or CP conditioned media, produce significant quantities of neurotrophic factors and growth factors capable of enhancing the growth and survival of non-CP cells, including neuronal and non-neuronal cells, in cell culture. In addition, the experiments demonstrate that a CP preparation can protect neurons from serum deprivation-induced cell death. The CP preparations are further capable of stimulating and/or maintaining the neuronal neurite processes in neuronal cells that are essential for central nervous system networking that underpins all brain activity. Although the response to the CP conditioned media supplement did not exceed the response to serum in Example 2, the protein concentration in this media is less than 1% of that in the serum supplement and thus is an extremely potent agent. These experiments demonstrate that CP preparations as defined herein are able to enhance the serum survival and function of neuronal and non-neuronal cells in vitro.

Industrial Application

The present invention is particularly useful in enhancing the growth and survival of non-CP cells in long term or short term culture. Such non-CP cells may comprise cells or tissues which have been obtained from a donor and which are maintained in short-term culture prior to transplantation to a recipient. Alternatively, the non-CP cells may comprise primary or secondary cell cultures or cell lines including immortalized cell lines for in vitro experimentation.

It is not the intention to limit the scope of the invention to the abovementioned examples only. As would be appreciated by a skilled person in the art, many variations are possible without departing from the scope of the appended claims.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

What we claim is:

1. A method for enhancing growth, survival and/or maintenance of function of non-choroid plexus (non-CP), non-neuronal cells in long term or short term culture, wherein the non-CP, non-neuronal cells are islet cells, fibroblasts or Human Umbilical Vascular Endothelial Cells (HUVEC) cells, said method comprising the steps of:

(a) providing a choroid plexus (CP) preparation, wherein the preparation comprises:
1) a CP cell population capable of producing one or more factors that support survival and growth of non-CP, non-neuronal cells; and/or
2) a CP cell culture capable of producing one or more factors that support survival and growth of non-CP, non-neuronal cells; and/or
3) CP conditioned media from a) or b) comprising one or more factors that support survival and growth of non-CP, non-neuronal cells, alone or in combination with a culture medium suitable for growth survival and/or maintenance of function of non-CP, non-neuronal cells to produce a.an enhanced medium; and
(b) culturing the non-CP, non-neuronal cells in the enhanced medium of step (a).

2. The method of claim 1, wherein the non-CP, non-neuronal cells are cultured for a short term prior to transplantation into a recipient.

3. The method of claim 2, wherein the non-CP, non-neuronal cells are islet β-cells, cultured prior to implantation into a recipient for use in the treatment of diabetes.

4. The method of claim 1, wherein the non-CP, non-neuronal cells are obtained from a different species to the cells of the CP preparation.

5. The method of claim 4, for enhancing the growth and survival of non-CP, non-neuronal cells that are to be used in xenotransplantation.

6. The method of claim 1, wherein the non-CP, non-neuronal cells are in a quiescent state before being cultured with the CP preparation.

7. The method of claim 6, wherein the non-CP, non-neuronal cells are freeze dried or frozen.

8. The method of claim 1, wherein one or more factors capable of supporting the survival and growth of non-CP, non-neuronal cells are selected from the group consisting of neurotrophins, growth factors, vascular endothelial growth factor, trophic factors, cytokines, mitogens, matrix cell support factors, enzymes, proteases capable of degrading toxic protein precipitates and proteins capable of complexing toxic metal ions.

9. The method of claim 8, wherein the enzymes are selected from proteases, alpha-1 antitrypsin, amylase, lipases, sucrase, lactase, and maltase.

10. The method of claim 8, wherein the protein capable of complexing toxic metal ions are selected from transferrin and ceruloplasmin.

11. The method of claim 1, wherein the CP cells of a) and/or b) include a purified population of CP cells and/or CP-derived cells selected from the group consisting of glial or glial-derived cells, epithelial cells, multipotent neuronal precursor cells, progenitor cells, and cells positive for a neuronal precursor cell marker.

12. The method of claim 11, wherein the neuronal precursor cell marker is neu-N.

13. The method of claim 1, wherein the CP cells are obtained directly from a) a suitable mammalian donor, b) a primary or secondary CP culture, c) a CP cell line including an immortalised CP cell line, or from a combination of any of a), b) and c).

14. The method of claim 13, wherein the CP cells in culture have been genetically modified.

15. The method of claim 13, wherein when the CP cells are obtained directly from a donor, they are included in cerebro spinal fluid.

16. The method of claim 1, wherein the CP and/or non-CP cells include isolated cells or clusters of cells and are free or encapsulated.

17. The method of claim 16, wherein the CP and non-CP, non-neuronal cells are free to make direct contact with one another, or they are free but separated by a biocompatible separation means which allows the diffusion of secreted factors from the CP cells to the non-CP, non-neuronal cells.

18. A method of enhancing the growth, survival and/or maintenance of function of non-choroid plexus (non-CP) non-neuronal cells in long term or short term culture, wherein the non-CP, non-neuronal cells are islet cells, fibroblasts or Human Umbilical Vascular Endothelial Cells (HUVEC) cells, said method comprising the step of incubating non-CP cells with a choroid plexus cell (CP) preparation comprising:
 a) a CP cell population capable of producing one or more factors that support the survival and growth of non-CP, non-neuronal cells; and/or
 b) a CP cell culture capable of producing one or more factors that support the survival and growth of non-CP, non-neuronal cells; and/or
 c) CP conditioned media from a) or b) containing one or more factors that support the survival and growth of non-CP, non-neuronal cells.

19. A method of protecting non-choroid plexus (non-CP) non-neuronal cells in culture from serum deprivation-induced cell death, wherein the non-CP, non-neuronal cells are islet cells, fibroblasts or Human Umbilical Vascular Endothelial Cells (HUVEC) cells, said method comprising the step of incubating non-CP, non-neuronal cells in a serum free media with a choroid plexus (CP) preparation comprising:
 a) a CP cell population capable of producing one or more factors that support the survival and growth of non-CP, non-neuronal cells; and/or
 b) a CP cell culture capable of producing one or more factors that support the survival and growth of non-CP, non-neuronal cells; and/or
 c) CP conditioned media from a) or b) containing one or more factors that support the survival and growth of non-CP, non-neuronal cells.

* * * * *